United States Patent [19]
Schlutz

[11] 3,982,691
[45] Sept. 28, 1976

[54] CENTRIFUGE SEPARATION AND WASHING DEVICE AND METHOD

[76] Inventor: Charles A. Schlutz, 7081 NW. 10th Place, Plantation, Fla. 33313

[22] Filed: Oct. 9, 1974

[21] Appl. No.: 513,509

[52] U.S. Cl. .................... 233/2; 233/14 R; 233/15; 233/21; 233/27
[51] Int. Cl.² .............. B04B 7/16; B04B 11/06; B04B 15/12
[58] Field of Search ............... 233/26, 27, 21, 1 R, 233/1 B, 1 D, 14 R, 14 A, 15, 16, 2

[56] References Cited
UNITED STATES PATENTS

| | | | |
|---|---|---|---|
| 1,429,320 | 9/1922 | Bouillon | 233/14 R |
| 3,096,283 | 7/1963 | Hein | 233/26 X |
| 3,326,458 | 6/1967 | Meryman et al. | 233/26 |
| 3,452,924 | 7/1969 | Schlutz | 233/14 R |
| 3,561,672 | 2/1971 | Schultz | 233/17 |
| 3,672,564 | 6/1972 | Schlutz | 233/26 |
| 3,674,197 | 7/1972 | Mitchell et al. | 233/14 R |
| 3,724,748 | 4/1973 | Jacobson | 233/27 X |
| 3,744,975 | 7/1973 | Mailen | 233/26 X |
| 3,825,175 | 7/1974 | Sartory | 233/2 |
| 3,864,089 | 2/1975 | Tiffany et al. | 233/26 |

Primary Examiner—George H. Krizmanich
Attorney, Agent, or Firm—Murray and Whisenhunt

[57] ABSTRACT

A centrifuge device and method are provided for separating and/or washing finely-divided solid particulate material suspended in a liquid. The invention is especially useful in so treating blood. The centrifuge forms a dense suspension of blood cells in a plurality of blood cells receiving means evenly spaced about the periphery of a rotatable enclosure. The receiving means have converging walls which at their juncture form a locus of maximum centrifugal force. Wash liquid is passed through the dense suspension of blood cells counter to the direction of the centrifugal force by entry into the blood cell receiving means at the locus of maximum centrifugal force. Independent conduits connect the locus of maximum centrifugal force through an injector to a supply for the wash liquid and, after fully resuspending the blood cells in a suitable resuspending liquid, the resuspended cells exit from the centrifuge via the independent conduits and injector, which have also therefore been washed by the wash liquid. Thus recontamination is avoided. A unitary disposable structure including the enclosure, blood cell receiving means, conduits and injector is also provided.

26 Claims, 10 Drawing Figures

CENTRIFUGE SEPARATION AND WASHING DEVICE AND METHOD

The present invention relates to a centrifuge device and method for separating and/or washing finely-divided solid particulate material suspended in a liquid. The device has particular applicability where the solid particulate material must be substantially completely recovered or where the particulate material must be washed or otherwise treated in an isolated environment, for example, in a sterile environment. Thus, the invention has particular utility in separating and/or washing biological particulate material suspended in a liquid. As a preferred embodiment, the invention relates to an apparatus and method for washing blood.

BACKGROUND OF THE INVENTION

Centrifuge devices and methods of the present nature have been known in the art. These devices and methods are, generally, characterized by their abilities to separate and/or wash very finely divided particulate material suspended in a liquid where that particulate material is to be substantially conserved and/or where that particulate material must be separated or washed in an isolated environment. Devices and methods of this nature, therefore, have their greatest utility in connection with the separating and/or washing of blood and that is also the preferred embodiment herein. Thus, while the invention is of broader applicability as indicated above, the invention will be primarily described in terms of this preferred embodiment for the sake of conciseness.

As is well known, human blood obtained from volunteer donors often contains constituents which should not be transmitted into the blood stream of the blood recipient. While it is possible to identify blood having these unwanted constituents, it is difficult to remove those constituents from the blood and the blood is often rendered useless or can be used only for less critical application, such as the production of plasma and the like.

The art has proposed various devices and methods for washing blood to remove unwanted constituents such as contaminants, toxicants, viruses, medicants, glycerines and the like. Many of these devices and methods center around an operation for separating the blood cells, especially the red blood cells, from the plasma and, after washing the blood cells, resuspending the cells in uncontaminated plasma or other suitable blood cell resuspending liquid. This is particularly useful for blood bank purposes where common viruses, such as hepatitis viruses, are washed from the blood and the washed blood can then be used in the blood bank. In another mode of use, blood containing unwanted medicants, such as barbituates and the like, can be washed and returned to the donor/patient. Similarly, allergens and serum proteins can be washed from blood. Also, the devices and methods can be used to deglycerinate previously frozen but thawed whole blood (frozen blood has glycerin added thereto). Or cellular debris can be removed from whole blood since particles of different densities will form different layers in a centrifuge as is well known. Other similar kinds of separation and/or washing operations can be performed with these known devices and methods.

While a wide variety of devices and methods have been proposed in the art, the most successful devices are based upon a centrifugal separation of the blood cells from the plasma, with subsequent counter-flow washing of the blood cells. For example, whole blood is placed in a centrifuge device, which, when revolving, forces the cells into discrete areas where the blood cells are compacted. Thereafter a washing solution, such as a sterile saline solution, is passed through the compacted blood cells to wash those cells of unwanted constituents, as indicated above.

The general arrangement and operational requirements of such known devices and methods are disclosed in U.S. Pat. No. 3,347,454 issued to the present inventor. However, the devices and methods of that patent require that the components of the device which actually contact blood be either entirely replaced or completely cleansed after each use, since a batch of contaminated blood could pass a portion of those contaminates to a succeeding batch of blood processed in the device, if replacement or cleansing of the device is not performed. Further, the device is of a batch operation character and can process blood only at a relatively low throughput per unit time.

It was recognized that improvements in the ability to wash succeeding batches of blood were desired and U.S. Pat. No. 3,561,672, issued to the present inventor, provides an improvement of that nature. That patent provides disposable receptacles which can receive a plurality of batches of blood for simultaneous washing in a single centrifuge operation. Independent and adjustable pressure heads for each of the plurality of batches within the centrifuge are provided to control the flows of wash liquid through the respective batches of blood. The disposable units include the blood receptacles, associated conduits and seal devices. The operation of this device is described in some detail in *CONTINUOUS FLOW CELL WASHING SYSTEM*, Schultz and Bellamy, TRANSFUSION, Volume 8, No. 5, September-October, 1968, and a pre-packaged combination of two receptacles, associated seal devices and conduits is described in detail in *A Disposable Counterflow System for Washing Erythrocytes in a Centrifugal Field*, Schlutz and Bellamy, Proc. 12th Congr. Int. Soc. Blood Transff., Moscow 1969 Bibl. Haemat., No. 38, Part II, pp. 350–358 (Karger, Basel, 1971).

Thus, the art has available considerable details of operation, construction and associated equipment for centrifuges of the present nature and those details will not be repeated herein. The entire disclosures of the above noted patents and publication are incorporated herein by reference and relied upon for the aforementioned details.

While this ability to provide a disposable package and sterilized component system for washing blood is the basis of one of the most successful commercial uses of a blood washing apparatus, that arrangement has the disadvantage that only a relatively low number of separate receptacles can be conveniently handled without so severely complicating the disposable unit, the apparatus and the associated equipment as to make the device and method impractical. Indeed, the commercial embodiments thereof contained only two blood receptacles, along with their associated seals and conduits. This results in a relatively low throughput of blood in a time period.

OBJECTS OF THE INVENTION

Therefore, in view of the above, it is an object of the invention to provide devices and methods wherein centrifugal separation and/or washing operations can be performed with a plurality of solid particulate receiving receptacles and wherein a continuous separation and/or washing operation may be performed. It is another object of the invention to provide devices and methods of the foregoing nature which are particularly adapted for the separation and/or washing of blood cells, especially red blood cells, or other blood fractions. It is a further object of the invention to provide devices and methods of the above nature wherein a plurality of blood cell receiving receptacles are part of a unitary disposable structure. It is a further object of the invention to provide such disposable structure of a design and configuration that it can be relatively cheaply manufactured and conveniently placed in and removed from a centrifuge apparatus. Other objects will be apparent from the following disclosure and claims.

BRIEF DESCRIPTION OF THE INVENTION

Briefly, the present invention provides a centrifuge apparatus and method wherein finely-divided solid particulate material, especially biological particulate material such as blood cells, may be separated and/or washed. The centrifuge apparatus provides means for rotating and thus centrifuging the solid particulate material, whereby the particulate material is collected in discrete areas in the form of a dense suspension under the centrifugal force exerted in the centrifuge. This separation of the particulate material also allows a washing step to be performed. A liquid, less dense than the particulate material, may be passed through the dense suspension of particulate material from the outermost periphery toward the axis of rotation of the centrifuge. This provides an important feature of the present invention where all parts of the particulate material are subjected to the flow of the liquid therethrough as opposed to arrangements in the prior art. This is especially useful in washing contaminants from blood, e.g., whole blood, and the invention will be illustrated with that embodiment.

The centrifuge apparatus for separating and washing blood comprises an enclosure means for enclosing and biologically isolating a quantity of blood cells in a suspending liquid, e.g., plasma or other suspending liquid. A rotation means is provided for rotating the enclosure means about its longitudinal (e.g., vertical) axis. This establishes a centrifugal force in the transverse (horizontal) direction of the enclosure means, which force is greatest at the periphery of the enclosure means. An injector means is provided for moving liquids into and out of the enclosure means. These liquids include the liquid suspended blood cells and the wash liquids. The injector means moves the liquids in and out of the enclosure means in a manner which keeps the system biologically isolated, e.g., sterile. A seal means is provided for sealing the injector means to the enclosure means in a liquid tight relationship. Thus, liquids can be moved into and out of the rotating enclosure means by way of the injector means because of the liquid tight seal which seals the injector means to the enclosure means. Accordingly, a continuous washing system can thereby be provided.

As a very important feature of the invention, there is provided a plurality of angularly shaped blood cell receiving means which are evenly spaced about the longitudinal periphery of the enclosure means. Any number of such receiving means may be used, e.g., 2 to 100 or more, especially 4 to 12, and particularly 6 to 8, so long as the receiving means have approximately equal radians or parts thereof between each adjacent receiving means in order to provide acceptable balance in the rotating centrifuge. These angularly shaped blood cell receiving means form at least a part of the outer periphery of the enclosure means. To provide the angular shape, there must be at least one pair of opposed wall portions of the blood cell receiving means which converge toward the longitudinal periphery of the enclosure means. Any number of pairs of converging wall portion may be used, e.g., from 1 to 100 or more, i.e., a conical shape of the receiving means has an infinite number of converging wall portions. However, in non-conical shapes 1 to 10 pairs, especially 2 to 6 pairs are preferred. At or about the apexes formed by juncture of the converging wall portions, there is established a locus of maximum centrifugal force in the rotating enclosure. Thus, the blood cells will be separated from at least some of the plasma and, thus, at least form a dense suspension in this angularly shaped receiving means and the maximum density of the suspension will be at the locus of maximum centrifugal force. The angles of convergence can effect the efficiency of separation of blood cells from plasma and, thus, the density of the suspension of the blood cells. Angles between 20° and 135°, especially between 35° and 115° are preferred. Usually, angles less than 90° will be used. Within these ranges of angles (along with the angular speed of rotation) the density of the suspension may vary considerably. In any case, however, the blood cells are compacted (i.e., contained in a small volume) and for the sake of simplicity the compaction will be hereinafter referenced.

As another important feature of the invention, there is provided a plurality of independent conduit means, each of which has one end connected to the injector means and the other end connected to the locus of maximum centrifugal force in the angularly shaped blood cell receiving means. Thus, there is provided an independent and separated fluid passageway from the injector means to the locus of maximum centrifugal force.

Power means for rotating the rotation means and enclosure means are provided. The speed of angular rotation should be sufficient to separate the blood cells from the suspending liquid and compact the blood cells in the blood cell receiving means.

Control means are provided for controlling liquid flows through the injector means, conduit means, blood cell receiving means and enclosure means. The control means allow for the flowing of suspended blood cells into each of the blood cell receiving means, for the flowing of a wash liquid through each of the said conduit means and then through the compacted blood cells in each of the blood cell receiving means, for the flowing of a resuspending liquid into the enclosure means and into the blood cell receiving means and for the flowing of resuspended blood cells from each of the receiving means through each, respective, conduit means, through the injector means and out of the centrifuge apparatus.

The power means and control means are conventional apparatus in the art and function in their conventional manners.

With the foregoing arrangement, the basic operation of the method and apparatus is as follows. Red blood cells in a suspending liquid, such as plasma or artificial plasma, are flowed through the injector means, then through the conduit means and into the blood cell receiving means of the enclosure. Since each of the angularly shaped blood cell receiving means is independently connected to the injector by the plurality of respective conduit means, a plurality of receiving means can be simultaneously filled with suspended blood cells. Thus, the centrifuge apparatus can be loaded with the blood while the centrifuge is rotating. Indeed, the rotation of the enclosure means (with the plurality of blood cell receiving means) helps to distribute the blood essentially evenly within the plurality of receiving means. After sufficient centrifugal force is generated on the suspended blood cells, the heavier solid particulate blood cells will be forced toward the locus of maximum centrifugal force and compacted in that region. The suspending liquid, on the other hand, will be displaced from the locus of maximum centrifugal force and toward the axis of rotation of the enclosure means. After that separation has been accomplished by sufficient centrifugal force, then the blood cells can be washed by flowing a wash liquid through each of the said conduit means and then through the blood cells in each of the blood cell receiving means. Here again, the wash liquid is displaced from the locus of maximum centrifugal force towards the axis of rotation of the enclosure means. Thereafter, the blood cells are resuspended in a liquid and removed from the apparatus. Of course, as described above, the injector means is at the axis of rotation and is provided with means for moving the wash liquid and resuspending liquid from the enclosure means and to the outside of the centrifuge apparatus.

As another important feature of the invention, after the washing has taken place as described above, the washed blood cells can be removed from the blood cell receiving means through each of the respective conduit means and subsequently through the injector means and out of the centrifuge apparatus, while the centrifuge apparatus is being rotated. This may be accomplished, among other ways, simply by flowing a liquid through the injector means and through the enclosure means which thereby forces the compacted and washed blood cells from the receiving means, through the conduit means and out of the centrifuge apparatus via the injector means. Of course, when the blood cells are so "unloaded", the rotational speed of the centrifuge is considerably reduced, e.g. below 400 RPM. This counter flow of liquid is accomplished simply by placing a greater pressure head on the counter flowing liquid than the pressure developed by the lower rpm's of the centrifuge during that "unloading" step. A pressure differential exerted by the resuspending liquid across the compacted blood cells of at least about ¼ pound will normally be used.

From the foregoing, it can be seen that the centrifuge can be continuously operated in that blood cells, suspended in natural plasma or artificial plasma, can be "loaded" into the centrifuge, separated by centrifugal force, washed, and "unloaded" from the centrifuge without the centrifuge ever being completely stopped. Only the difference in rotational speeds are required for the steps. This is possible since the washing step fully cleanses the injector means, conduit means and blood cells receiving means prior to the "unloading" step, so that the cleaned blood cells flow only through this previously cleaned path.

It should be further appreciated that since the washing liquid enters the receiving means, from the conduit means, at the point of maximum centrifugal force, the washing liquid passes through essentially all of the compacted blood cells, which is not the case with prior art arrangements, as discussed hereinbefore. As in those arrangements, the washing liquid could never be introduced into the locus of maximum centrifugal force and some amount of blood cells could never be fully washed by the washing liquid. Thus, a hazard of residual contamination was always present which caused concern for the "purity" of the washed blood and required a cleansing of the apparatus between batches.

Further, with the present arrangement, the number of blood cell receiving means may significantly exceed the two containers used in the prior art, as disclosed above. Indeed, a preferred form of the invention uses eight separate blood cell receiving means and thereby greatly increases the efficiency of the present arrangement over the arrangements of the prior art.

Also, by reason of the present arrangement, as discussed above, a disposable enclosure means with the blood cell receiving means can be provided and that arrangement allows for rapid removal of the disposable enclosure means. Thus, the enclosure means may be constructed of any inert material which can be releasably held by the rotation means of the centrifuge. In this regard, the rotation means will have at least one cavity therein for receiving and retaining enclosure means during rotation thereof. This will, of course, require that the cavity of the rotation means and the enclosure means have complementary shapes so that the enclosure means may be periodically removed from the cavity of the rotation means and replaced by a new enclosure means. Of course, with such an arrangement, it is most convenient that the enclosure means, the conduit means, the injector means and the sealing means form a replaceable and disposable unitary structure. In view of the intended disposable nature thereof the so produced unitary structure is preferably made, principally, of a moldable material, and especially an extendable material so that small differences in the complementary shapes of the disposable receiving means and the cavity in the rotating means can be compensated for by extension of the enclosure means. In other words, the shape of the unitary structure can therefore be conformed to the shape of the cavity in the rotation means by action of centrifugal forces on the unitary structure during the rotation thereof.

Other important features of the invention and advantages of the invention over the prior art will be apparent from the following detailed description of the invention.

DETAILED DESCRIPTION OF THE INVENTION

Figure 1:
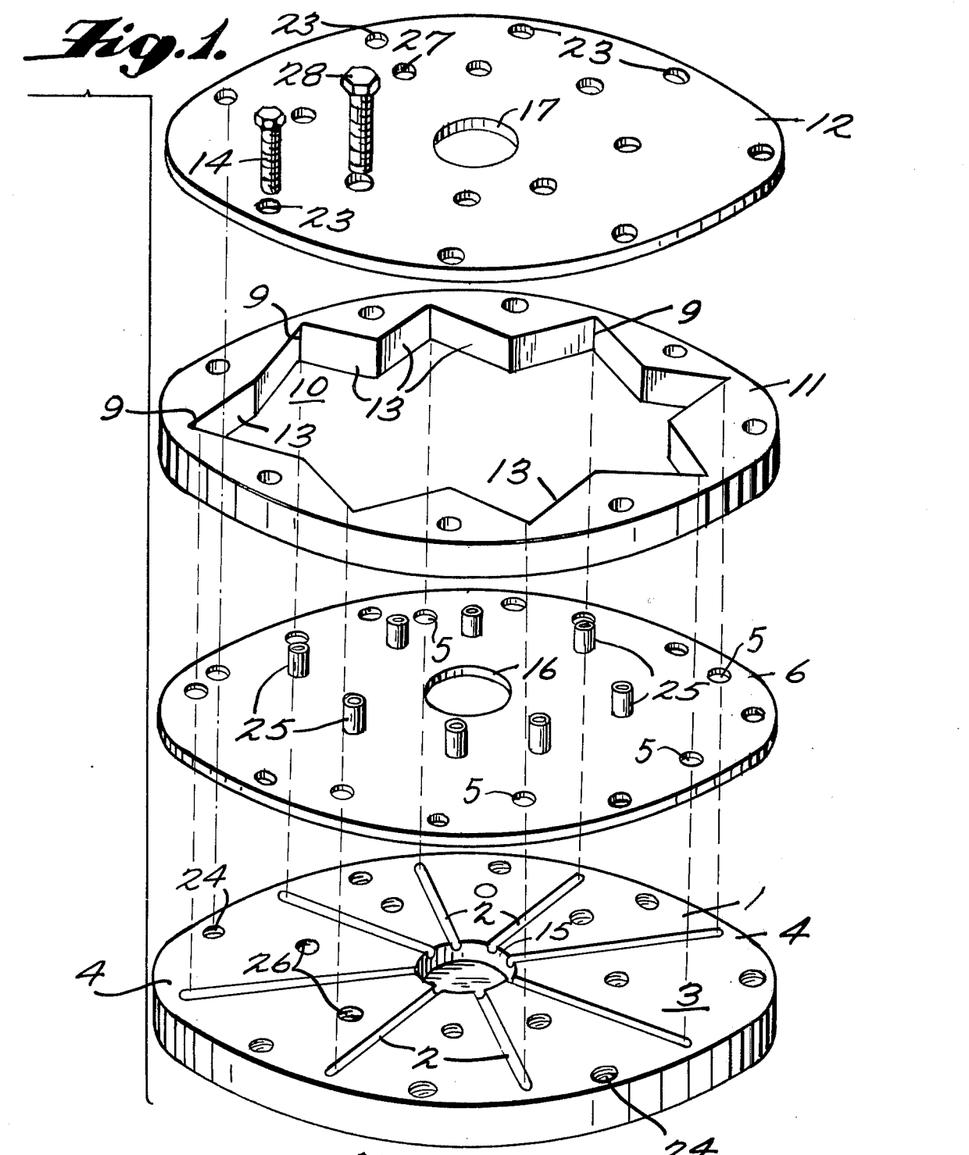
FIG. 1 is a perspective exploded view showing an embodiment of the invention, particularly with reference to the principles involved.

The invention can best be understood by specific reference to FIG. 1 where the principles of the invention are illustrated in terms of a specific assembly. The assembly of that embodiment is composed of four main assembly plates. Bottom plate 1 of the assembly has a plurality of recesses 2 in the top surface 3 of the plate. At the periphery 4 of bottom plate 1, the recesses 2 terminate in registry with openings 5 traversing through intermediate plate 6. When intermediate plate 6 is secured to bottom plate 1, the combination of plate 6 and recesses 2 will thereby form enclosed recessed conduits 2 leading from the openings 7 in rotating seal 8 (See FIG. 2) to the periphery of bottom plate 1.

Openings 5 in intermediate plate 6 are in registry with the apex 9 of each respective blood cell receiving means, generally 10, of receiving plate 11. When top plate 12 is secured to receiving plate 11, in combination with those two plates being secured to intermediate plate 6 and bottom plate 1, then blood cell receiving means 10 becomes part of an overall enclosed space defined by receiving plate 11, intermediate plate 6 and top plate 12, and especially the wall portions 13 of receiving plate 11.

The various plates, described above, can be attached by any suitable device, such as bolts 14 or the like. Rotating seal 8 (See FIG. 2) is disposed in and engaged in a liquidtight manner by the respective apertures 15, 16 and 17 in plates 1, 6, and 12. Openings 7 in rotating seal 8 are at a level and position corresponding to the level and position of conduits 2 in bottom plate 1, while openings 19 in rotating seal 8 correspond to the level and position, generally, of the center of the apexes 9 in receiving plate 11.

An injector 20 (See FIG. 3) is disposed within rotating seal 8 (See FIGS. 3 and 4) to provide pathways for liquid flow into and out of seal 8 at levels corresponding to the openings 7 and 19. Accordingly, liquid flow pathways are established in the assembly from openings 21 in the injector 20, through the lower openings 7 of the rotating seal 8, through conduits 2, through openings 5 in intermediate plate 6, into the receiving means 10 of receiving plate 11, through the enclosure defined by plates 6, 11 and 12, through upper openings 19 of rotating seal 8 and out of injector 20 via openings 22.

Since the assembly will be rotated at relatively high angular speeds, it is necessary that the assembly be rather rigid and for this purpose a plurality of bolt holes 23 may receive a plurality of bolts 14 for threaded engagement into threaded holes 24 of bottom plate 1. Additional rigidity may be provided by stiffening annular rings 25 which correspond to openings 26 in bottom plate 1 and openings 27 in top plate 12 and are secured to the assembly by means of appropriate bolts 28 which pass through the assembly and are secured by nuts (not shown) on the underside of bottom plate 1. Rings 25 may be sealed against liquid flow out of top plate 12 or into the recesses of bottom plate 1 by "O" rings disposed in "O" ring receiving recesses at the top and bottom of rings 25 (not shown), if desired.

Figures 2, 3:
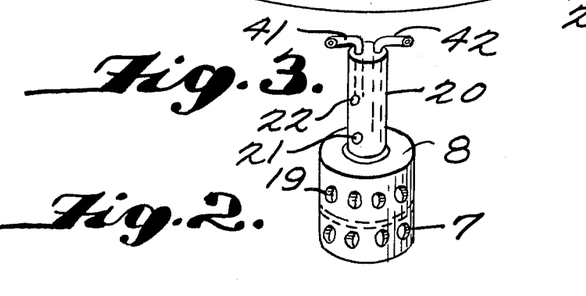
FIG. 2 is a perspective view of the rotating seal used in the assembly of FIG. 1.
FIG. 3 is a perspective view of the injector means used in the assembly of FIG. 1.
Figures 4, 6:
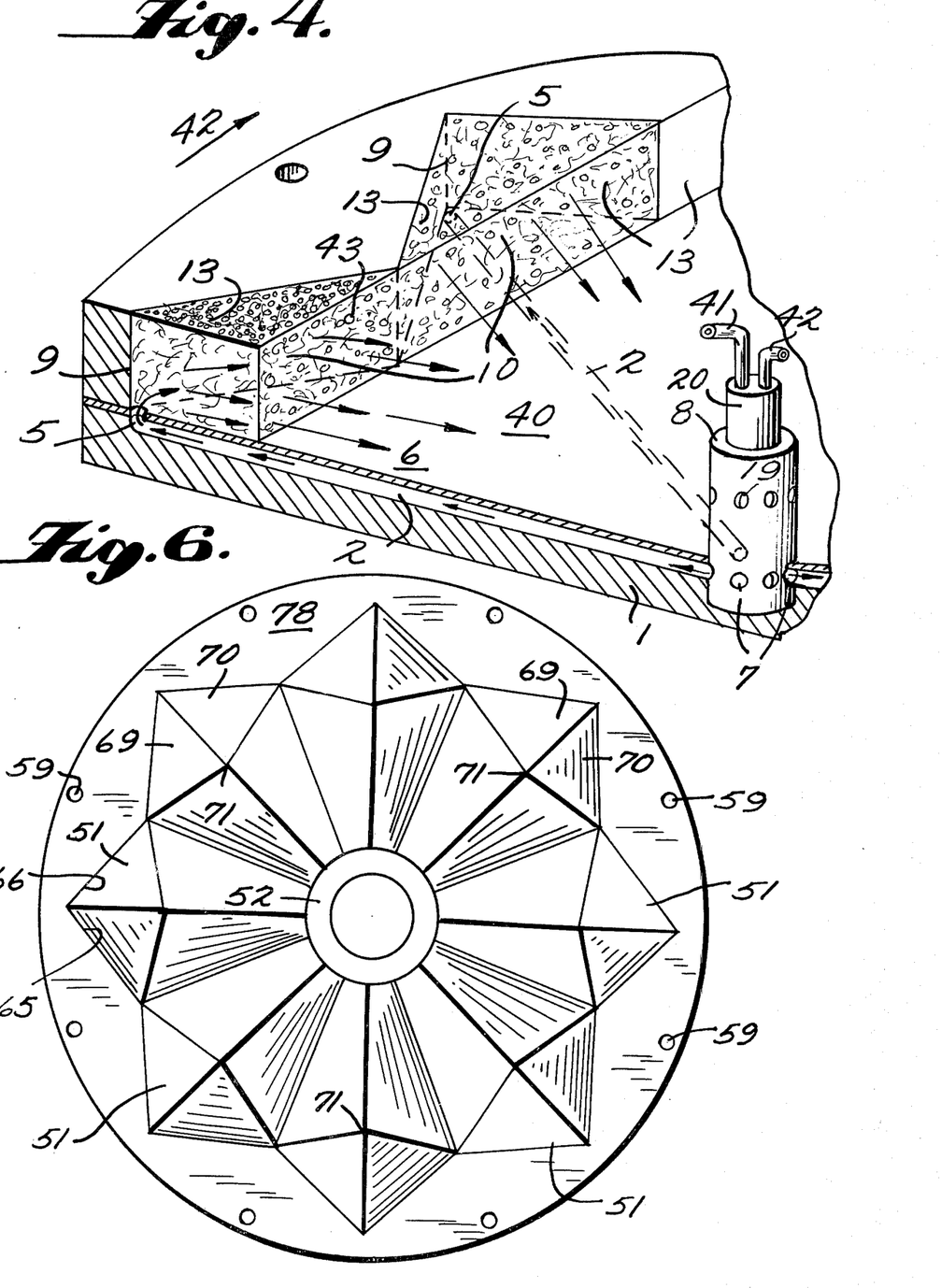
FIG. 4 is a broken cross-sectional view of a portion of the assembly of FIG. 1, and FIG. 4 further illustrates the principles of the invention.
FIG. 6 is a top view of the disposable enclosure means of FIG. 5.

The principles of operation of the assembly of FIGS. 1 through 3, and particularly as pertains to FIG. 1, can better be understood by reference to FIG. 4. In FIG. 4, bottom plate 1 has recessed conduits 2 therein, which conduits are enclosed at their upper portions by intermediate plate 6. The openings in intermediate plate 6 at 5 terminate at each apex 9 of converging walls 13. A fluid pathway, as described above, is provided through opening 7 of rotating seal 8, through conduit 2, through opening 5, through the enclosure generally designated as 40, out through opening 19 of seal 8 and out of the apparatus through pipe 41 of injector 20.

When the assembly is in rotation, at operational rpms, sufficient centrifugal force develops so that the solid particulate matter in the centrifuge collects in the receiving means, generally 10, bounded by converging walls 13. In this case, the blood cells are shown compacted in the receiving means 10 of the broken away portion shown in FIG. 4. The rotation is illustrated by arrow 42.

The compacted blood cells displace the plasma associated therewith towards the openings 19 of seal 8. When the separation of the blood cells has been sufficiently accomplished, a wash liquid can be introduced into injector 20 via pipe 42 and passes through openings 7 and conduits 2 as shown by the arrows. The wash liquid then passes through openings 5 and spreads out to wash the blood cells 43 compacted in receiving means 10. The wash liquid, thereafter, by virtue of a higher presssure head, passes through enclosure 40, out of openings 19 of seal 8, through injector 20 and out of the apparatus via pipe 41.

It will be appreciated that the blood cells 43 are of greater density than either the plasma normally associated therewith or the wash liquid which is subsequently used for washing the separated blood cells. Under the circumstances, the centrifugal force acting upon the blood cells will be greater than the centrifugal force acting upon either the plasma or wash liquid. Therefore, both the plasma and wash liquid can be passed through the blood cells, by means of an increased pressure head above the centrifugal force on the blood cells, since the more dense blood cells will cause displacement of the plasma or the wash liquid toward seal 8, the axis of rotation of the enclosure means, when the assembly is at operational rotational speeds.

It can also be appreciated from the assembly of FIG. 1 and the explanation thereof of FIG. 4 that with the present arrangement, the wash liquid is introduced at the apex formed at the juncture of the pair of oppositely disposed converging wall portions of the blood cell receiving means. With this arrangement, as opposed to prior art arrangements, the wash liquid will contact substantially all of the compacted blood cells. In prior arrangements, the wash liquid could only be introduced "close" to the locus of maximum centrifugal force, but those arrangements were not capable of introducing the wash liquid just at the locus of maximum centrifugal force. This was because the conduits were internal of the bag or container for enclosing the blood cells and the conduits could, therefore, not terminate at the point of maximum centrifugal force, since they would therefore be totally closed off.

With the arrangement of FIG. 1, however, other important advantages can be easily understood. Thus, the plurality of blood cell receiving means provides much greater efficiency than those of the prior art where only, generally, two different blood cell receiving compartments or bags were provided. Further, the plurality of independent conduit means of the present arrangement are cleaned during the washing process and the washed blood can be resuspended and passed back through those washed conduits, in a counter-flow direction, without contamination of the washed blood. Also, no independent flow path from the respective receiving means need be provided for removing the plasma and wash liquid from the enclosure means. Thus the enclosure means, essentially, is open to all of the receiving means and presents a more efficient use of pathways for removing plasma and wash liquid during operation of the centrifuge.

Figure 5:
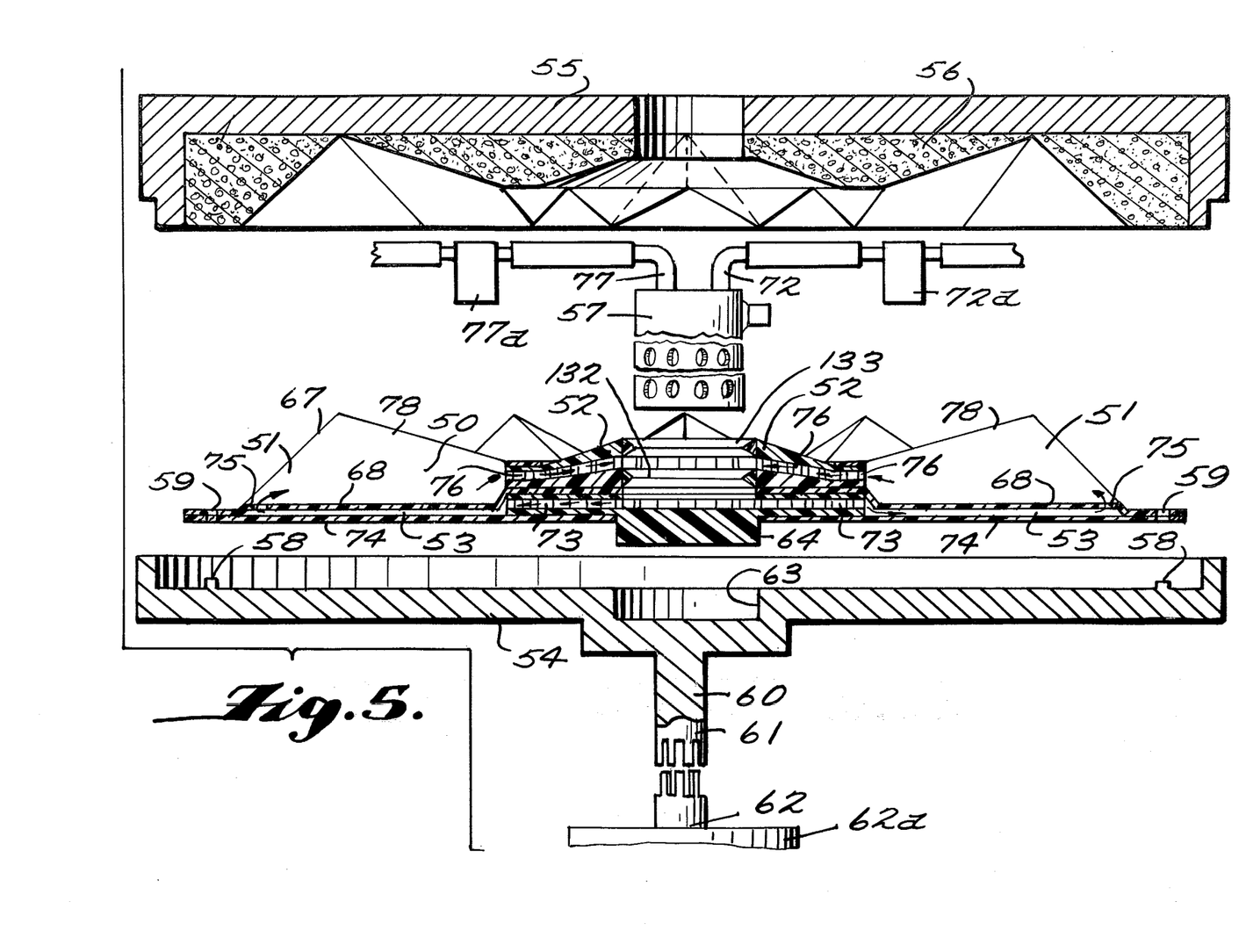
FIG. 5 is an exploded cross-sectional view of a preferred form of the invention wherein the enclosure means is disposable.

It will also be noted that while the arrangement has a pair of opposite wall portions which converge, intermediate plate 6 and top plate 12 are parallel and the wall portions of the blood cell receiving means formed by those plates do not converge. Particularly for the two foregoing reasons, a preferred embodiment of the invention is shown in FIG. 5. The arrangement of FIG. 5 differs from the arrangement in FIG. 1, principally, in the particular shape of the enclosure means, the form of the rotational means and the specific shape of the blood cell receiving means. Also, the enclosure of FIG. 5 is disposable, but it should be appreciated that a disposable enclosure in the basic configuration of FIG. 1 may be used. Otherwise, the general flow paths and operational characteristics of the preferred arrangement of FIG. 5 are similar to those of FIG. 1, particularly as explained in FIG. 4.

In FIG. 5 there is shown a disposable enclosure means, generally 50, consisting of a blood cell receiving means, generally at 51, and an integral seal means, generally at 52. The disposable structure has independent conduit means 53, which corresponds to the conduit means 2 of FIG. 1. The rotational means is comprised of a lower platen member 54 and an upper platen member 55 having a hardened but replaceable and castable material 56 disposed therein, e.g., cement, plaster, polyester, or epoxy reinforced plastic and the like. The shape of the castable material conforms generally to the shape or configuration of the disposable enclosure means 50 (the upper portion thereof). Of course, the orientation of platens 54 and 55 are disposable enclosure 50 can be reversed, i.e., castable material 56 can be in bottom platen 54 and the outside orientation of disposable enclosure means 50 is reversed. Since the disposable enclosure means 50 carries its own integral seal 52, no permanent seal, corresponding to seal 8 of FIG. 1, is needed in this embodiment. An injector means 57 (shown in a broken view) corresponds to the injector means 20 of FIGS. 1, 3, and 4, but is also disposable. The operation of the injector means is the same as described therein, although the specific special arrangement of the pipes are somewhat different to accommodate the integral seal 52 of disposable enclosure 50, as shown in FIG. 5. Lower platen member 54 has a plurality of upstanding indexing projections 58 which correspond to indexing holes 59 in disposable enclosure 50. These simply index the disposable enclosure correctly within the cavity formed between lower platen member 54 and upper platen member 55 when the two platen members are secured together. Lower platen member 54 has a rotor base 60 which is attached by any convenient means such as splines and the like 61 to a drive shaft 62 and power means 62(a), e.g., an electric motor. Seal means 52 is held in recess 63 of lower platen member 54 by means of seal projection 64. Seal projection 64 also forms a support for injector means 57.

With particular reference to FIG. 6, which is a top view of the disposable enclosure and seal means, it will be seen that the blood cell receiving means, generally 51, has oppositely disposed converging wall portions 65 and 66, in a manner similar to that of FIG. 1. However, additionally, the top and bottom wall portions 67 and 68 (see FIG. 5) also form an angle, i.e., converge. Further, as shown in FIG. 6, wall portions 69 and 70 converge from pinnacle 71. Thus, there are multiple pairs of opposite wall portions which converge toward a locus of maximum centrifugal force, in the arrangement of FIG. 5, and this effects a multiplication of the efficiency of the centrifugal force exerted on the blood cells within the blood cell receiving means 51. This, of course, is a very advantageous feature of the present invention.

The flow paths in the arrangement of FIG. 5 are quite similar to the flow paths described in detail in connection with FIGS. 1 and 4. Thus, the blood is pumped through pipe 72 (via control means 72a) of injector 57 and through a multiplicity of ports 73 in seal 52 into the respective conduits 53 formed between members 68 and 74. The conduits terminate at openings 75 at the locus of maximum centrifugal force. The openings 75 communicate conduits 53 with the blood cell receiving means, generally 51. The enclosure then provides a pathway to discharge ports 76 which communicate through seal 52 to injector 57 for passageway through the injector and out of discharge pipe 77 (via control means 77a).

The disposable enclosure 50 is therefore replaceable within the cavity formed by lower platen member 54 and upper platen member 55, simply by removing injector 57 and separating upper platen member 55 from lower platen member 54. The disposable enclosure 50 and seal 52, then lift off of lower platen member 54 and can be discarded. The disposable enclosure and seal are a unitary structure consisting of the blood cell receiving means 51, the enclosure means, generally 50, the seal means 52 and the conduit means 53. Since injector 57 is also disposable, no cleaning of the centrifuge is required, in the manner of FIG. 1.

Figure 7:
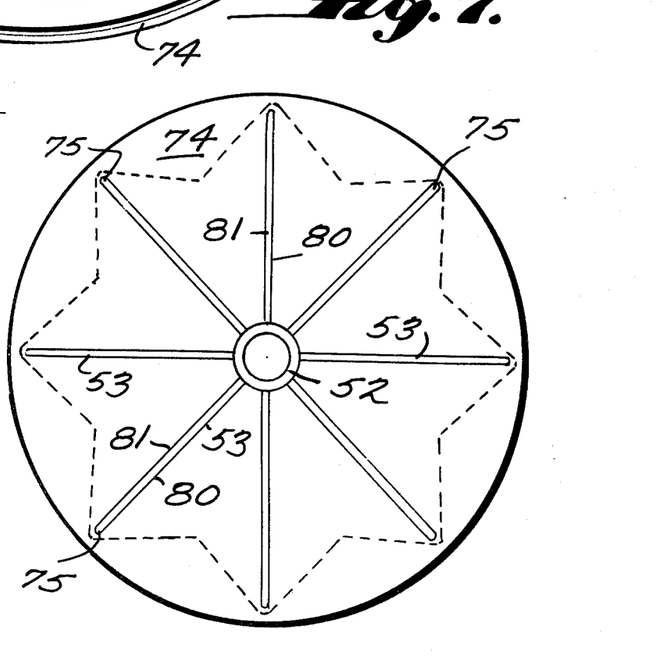
FIG. 7 is a bottom view of the disposable enclosure means of FIG. 5.

The convenience of the arrangement shown in FIG. 5 is most apparent and the disposable enclosure of the arrangement forms a very important feature of the invention. That enclosure, in a preferred embodiment, is made with three separate films (or members) of an inert material, e.g., plastics and the like. The first film or member 74 forms the bottom portions of conduits 53, while the second film or member 68 forms the top portions of conduits 53. The second film 68 also forms the bottom wall of enclosure 50. The third or top most film or member 78 completes the three films or members forming the disposable enclosure. Parallel but displaced liquid-tight seals 80 and 81, e.g., heat seals, between films 74 and 68 (See FIG. 7) form conduits 53 which terminate at openings 75. The shape of the top film or member 78 is normally accomplished by molding operation, such as a vacuum thermo-forming operation, in manners well known to the art.

Figure 8:
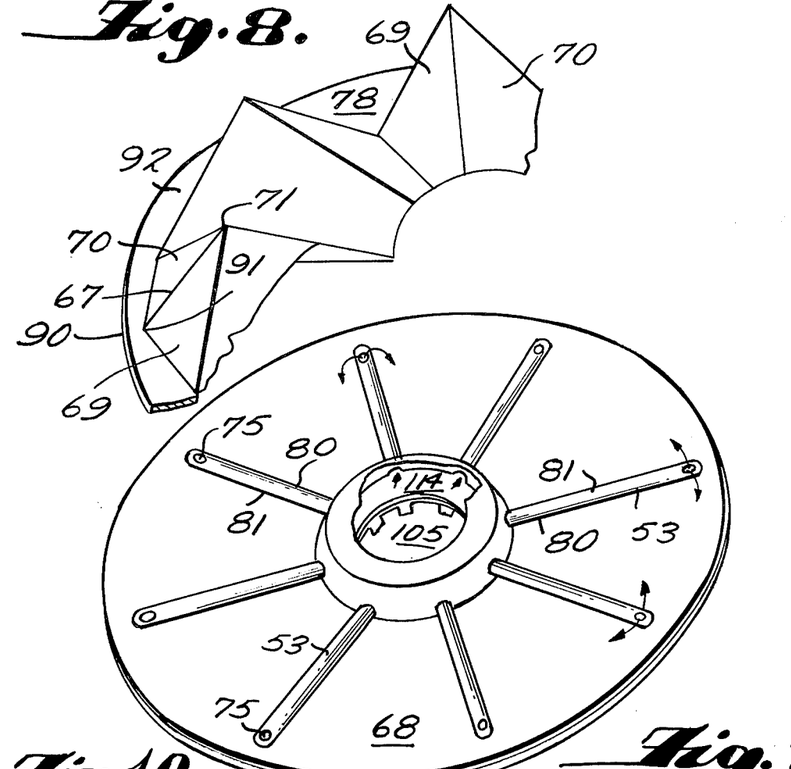
FIG. 8 is an exploded view of the disposable enclosure means of FIG. 5.

The arrangement and construction of the disposable enclosure can better be understood by reference to FIG. 8. In this embodiment, thermoplastic films are used for constructing the disposable enclosure. Thus, lower film 74 has placed on top thereof intermediate film 68. That intermediate film has a plurality of holes 75 punched therein and heat seals 80 and 81 form conduits 53 which terminate at holes 75. Upper film 78 has thermoformed thereinto converging wall portions 67, 69 and 70, which converge from apex 71 toward the periphery 90 of upper film 78. These wall portions converge at 91 to form a locus of maximum centrifugal force, when the disposable unit is rotated within the arrangement of FIG. 5. The periphery 90 is sealed (e.g., heat sealed) along the outer portion 92 of film 78 to form a unitary structure, in the manner illustrated in FIG. 5.

Figure 9:
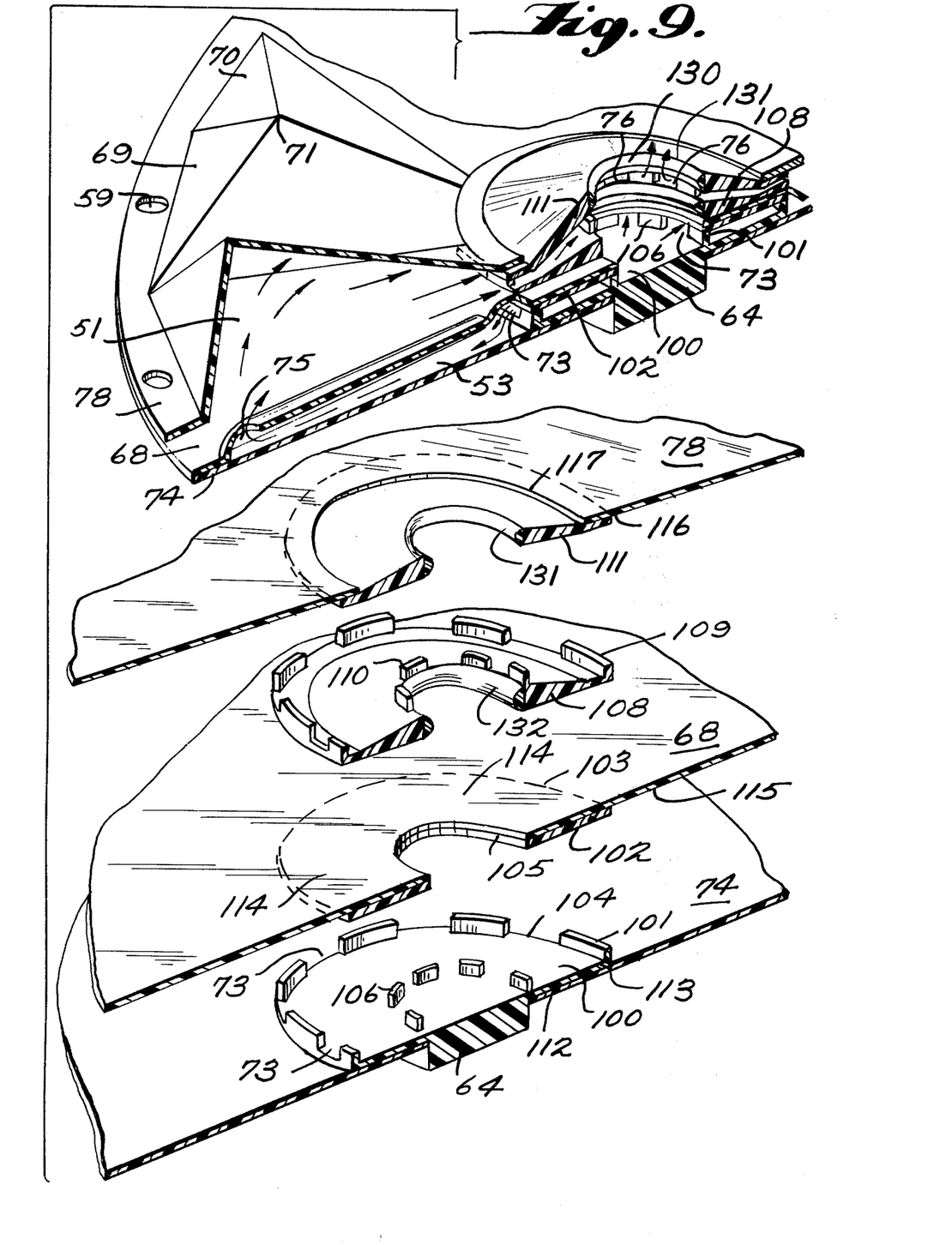
FIG. 9 is a partly sectioned and exploded view of the seal and films making up the disposable enclosure means of FIG. 5.

The seal means which completes the unitary disposable structure is shown partly in cross-section and in exploded view in FIG. 9. The seal comprises base plate 100 having outer projections 101 around the periphery thereof. Intermediate plate 102 is configured such that its outer periphery 103 conforms to the outer periphery 104 of base plate 100. The inner periphery 105 of intermediate plate 102 is configured in a diameter equal to interior projections 106 of base plate 100. Similarly, outer projections 101 are so positioned around the periphery of base plate 100 so as to contact the undersurface of intermediate plate 102 near the outer periphery 103 thereof. This arrangement between base plate 100 and intermediate plate 102 provides a chamber between base plate 100 and intermediate plate 102 with a multiplicity of flow ports 73, for appropriate flow of liquid into conduits 53 and then into blood cell receiving means 51.

A similar arrangement is provided for an exit flow path. Thus, top plate 108 has similarly arranged top plate intermediate and outer projections 109 and 110, respectively, which cooperate with the top cover plate 111 to produce flow ports 76, for appropriate flow of liquid from the blood cell receiving means 51 (See FIG. 5).

As noted above, the seal, enclosure, and conduits form a unitary structure which is disposable. The enclosure and conduits are made, as discussed above, by heat seals and thermoforming of the films 74, 68 and 78. The enclosure and seal are then assembled as a unitary structure by appropriate placement of base plate 100, intermediate plate 102, top plate 108 and top cover plate 111 between films 74, 68, and 78. Thus, the undersurface 112 of base plate 100 fits over the innermost peripheral edge of film 74 in the area generally at 113 of FIG. 9. Intermediate plate 102 then is assembled onto base plate 100, in the manner described above, and toward the outer periphery 103 of intermediate plate 102, generally at 114, film 68 is placed such that the underside of the film, generally 115 of FIG. 9, overlays the outer periphery 114 of intermediate plate 102. Thus, the conduits are in communication with the ports 73 of the sealing device. Film 68 is then held in place and clamped between intermediate plate 102 and top plate 108. Top cover plate 111 is then assembled onto top plate 108. The underside of the innerperiphery of film 78, generally at 116, of FIG. 9, is placed over the outer periphery, generally at 117, of the top cover plate 111 of FIG. 9.

The assembly of the conduits, enclosure and seal is then formed into a unitary structure by causing base plate 100, intermediate plate 102, top plate 108, top cover plate 111 and films 74, 68, and 78 to be interlocked, as by adhesion, into a single unitary structure. The interlocking can be by any desired means, such as gluing with an adhesive, heat or solvent sealing or other adhesion or fusion. Alternately, frictional engagement and the like may be used. It is preferred, however, that the integral and unitary structure be interlocked by at least an adhesive or heat seal between the interlocking elements, as described above. Of course, the particular method and arrangement of assembling the unitary structure of the disposable enclosure with the seal is not at all critical and may be practiced as desired. The foregoing simply illustrated a suitable method for manufacturing of the unitary structure. The films are preferably made of a polymeric material, e.g., of plastic resins, such as a polyolefin (polyethylene, polypropylene, polypentene), polyvinyl chloride, polyvinylidene chloride, polyvinyl acetate, polystyrene, polyacrylate (such as polymethyl methacrylate), polyester, polyamide (such as nylon 6 or nylon 66) a polysiloxane, polycarbonate, polyacetate or butyrate, natural or synethic rubbers and combinations thereof. Similarly, the seal elements may be made of such polymeric materials. Preferably, the films and seal elements are made of a thermoplastic polymeric material, although this is not required. Any of the foregoing polymers can be used in producing the seal elements, but relatively low friction polymers are preferred, especially polyamides and polyolefines. Additionally, at least the inner-periphery of the seal can be made of or coated with a polytetrafluoroethylene resin to further reduce friction between the seal and the injector, since the seal must spin in a liquid-tight engagement with the injector.

Figure 10:
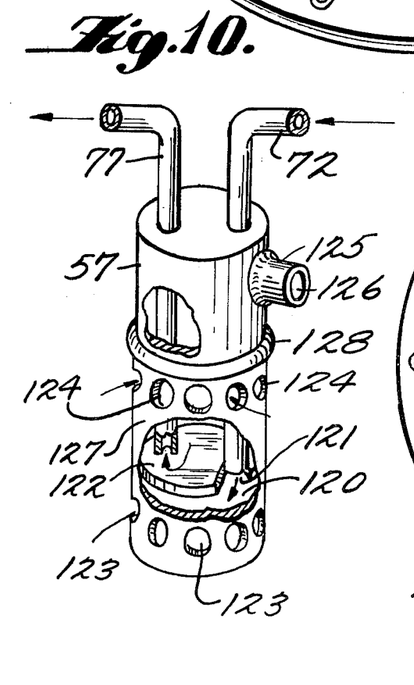
FIG. 10 is a partly broken and cross-sectional view of the injector means used with the disposable enclosure means of FIG. 5.

The injector is shown in FIG. 5 and it will be seen that there is a liquid-tight but slidable engagement between the inner periphery of seal 52 and the outer surface of the injector 57. The injector may be simply in cylindrical form as shown in FIG. 10. In that arrangement, injector 57 has an entry pipe 72 for conveying blood and/or wash liquid into the lower portion 120 of the injector 57 via opening 121 in divider plate 122. The fluid passes out of the injector via entry ports 123 and into the seal, as shown in FIG. 5, to pass through the seal by way of entry ports 73 into conduit 53. The wash liquid, which has been passed through the compacted blood cells, passed through the enclosure generally at 50, into discharge ports 76 of the seal and into discharge ports 124 of injector 57 (see FIG. 10). The wash liquid is then passed out of the injector and apparatus via exit pipe 77. A holder 125 may be fixedly attached to the injector for screwed engagement, or the like, via internal threads 126 for support of the injector in any desired means. Alternate supports for the injector may be provided, as desired. The injector may be made of any desired material, but one of the above noted polymers is preferred. The surface of the injector can be reduced in friction by application of a lubricant, such as silicone grease, or a polytetrafluoroethylene dispersion or the like. Additionally, if desired a sealing ring 128 may be retained in a corresponding recess on the outer surface of the injector for sealing the injector against top cover plate 111 of the seal, generally at 130, as shown in FIG. 9. Alternatively, or in addition thereto, top cover plate 111 may have its own sealing ring or sealing portion 131 made thereinto. A similar sealing ring or portion 132 may be in top plate 108 to seal the respective chambers which open into ports 73 and 76. The sealing rings or sealing portions can be of any desired relatively low friction material, such as molded polytetrafluoroethylene, nylon and the like. Again, biologically inert greases such as silicone grease or petroleum jelly may be used as a lubricant for these sealing rings or portions. Also, such a lubricant can be placed on the portion of base plate 100 which will normally contact the base of the injector 57, to reduce the sliding friction therebetween.

While not shown in the drawings, the centrifuge apparatus will also have associated therewith reservoirs, pumps and receiving containers for flowing blood, wash water and the like into and receiving washed blood out of the apparatus. Of course, the apparatus will also have associated therewith a power means and driving mechanism, such as motors, speed controllers and the like, for rotating the rotation means and enclosure means with sufficient angular rotation to separate the blood cells from the suspending liquid (plasma) and compact the blood cells in the receiving means. Also provided are control means controlling the rotation of the centrifuge and the flow of the various liquids, as described above. For example, liquid flow control must be provided in conjunction with entry pipe 72 by control means 72a in a manner known to the art so that blood may be flowed into pipe 72 and thereafter wash liquid flowed into pipe 72. Similarly, out of discharge pipe 77 via control means 77a is passed wash liquid during the washing step, and blood cell resuspending liquid is flowed through pipe 77 (via control means 77a) and into the enclosure, for resuspending the blood cells and flowing the resuspended blood cells back out of the apparatus via conduit 53 and entry pipe 72. These associated devices, power sources and controllers are known to the art and need not be described herein. In this regard, reference is made particularly to the U.S. patents and publicatins mentioned hereinbefore.

In operation, the apparatus is provided with reservoirs of blood and washing liquid which can be sequentially directed into entry pipe 72, by appropriate and conventional flow control means 72a. A pump, biologically acceptable, forces blood from the reservoir into pipe 72, out of entry ports 73, through conduit 53 and into enclosure 50. The flow of the blood from the blood supply, of course, goes through each of the plurality of independent conduits into the enclosure. In this regard, the enclosure, as defined above, has a plurality of angularly shaped blood cells receiving compartments. These compartments are evenly spaced, as defined hereinbefore, about the longitudinal periphery of the enclosure. Also as discussed above, at least one pair of opposite wall portions of each of the compartments converge toward the longitudinal periphery of the enclosure. Likewise, as discussed above, the first ends of the conduits are in communication with the blood supply and the other end of the conduits are connected with the apexes of the converging wall portion of each of the blood cell receiving compartments.

The enclosure, held in the cavity of the centrifuge, is rotated at a first lower angular speed about its transverse axis to help in evenly distributing the blood within the enclosure. This can be a relatively low angular speed, and indeed can be practiced simply in bringing the centrifuge up to operational rotational speeds for separating the blood cells, as discussed below. In any event, after the rotation of the enclosure has commenced, the speed of angular rotation is increased until there is sufficient centrifugal force exerted on the blood whereby the blood cells, especially the red blood cells, are separated from the liquid portion of the blood (the plasma) and the red blood cells are compacted and relatively evenly distributed in the receiving compartments.

Once this separation of blood cells has been accomplished, a wash liquid is then flowed from a convenient wash liquid supply source, which is in communication with the first ends of the conduits, through the conduits, into the apexes of the converging wall portion of the compartments, through the compacted blood cells and through the enclosure. Of course, the wash liquid finally exits from the centrifuge through discharge pipe 77. This flow of wash liquid is continued until the red blood cells are washed substantially free of contaminants, as discussed above. It should also be noted that the washing liquid will similarly wash the enclosure, seal and discharge pipe 77 at that same time.

Thereafter, the angular speed of rotation of the enclosure is reduced so that the compact blood cells in the receiving compartments may be resuspended in a suitable resuspending liquid. The resuspending liquid for the blood cells is flowed into the enclosure by way of discharge pipe 77, through the seal, and resuspends the blood cells in the suspending liquid. The flow of the resuspended blood cells continues through opening 75 at the apex of the converging wall portions, through the conduit 53 and into a suitable collecting reservoir via the seal and entry pipe 72. If desired, the resuspended blood cells can be sucked from the receiving means by vacuum, since the flexible, plastic converging walls can collapse under the vacuum reduced pressure.

Thus, it will be appreciated that the washed blood cells are passed countercurrently back through the apparatus and in the pathway which has been fully washed by the wash liquid in washing the red blood cells. This avoids any chance of contamination of the washed blood and is an important feature of the method and apparatus of the invention. Additionally, it should be fully understood that the washing with the wash liquid commences as the wash liquid enters the compartment through opening 75. This opening is at the point of maximum centrifugal force and will therefore contact all parts of the compacted blood cells, as opposed to prior art methods and apparatus.

The particular angular speeds of rotation can vary considerably depending upon the specific diameters of the enclosure and compartments. Obviously, for larger diameter enclosures, sufficient centrifugal force will be developed at much lower angular speeds than will be required for smaller diameter enclosures. However, as an indication of appropriate speeds, sufficient centrifugal force will be developed in a 12-inch diameter enclosure when the angular speed is between about 1500 and 5,000 revolutions per minute, more often between 2,000 and 4,000 revolutions per minute, e.g., around 3,000 revolutions per minute. The temperature at which the process is carried out is not critical and may be carried out at any temperature above the freezing point or coagulation point of the blood and below the denaturing point of the blood. Generally, temperatures between about 40°F and 120°F are satisfactory, especially between about 60°F and 90°F. The process is operated under pressures generated by the centrifugal force and in combination with the head pressure exerted by the wash fluid during the washing step or by the resuspending liquid in resuspending the blood cells and passing the resuspended cells out of the apparatus. In these latter regards, it is only necessary to supply the wash fluid or resuspending fluid at head pressures (or vacuum for removing the resuspended blood cells) great enough to flow the wash fluid or the resuspended blood cells opposite to the centrifugal force for passing the wash liquid or resuspended blood cells out of the centrifuge. An adjustable pressure pump in this regard is desirable so that the pressure for causing such flows can be readily obtained with different rpms of operation.

As can also be appreciated, tandem arrangements of the enclosure means may be used if desired, either of the disposable or non-disposable arrangements. Thus, for example, a stack of two or more enclosure means, as described above, may be contained within a single or cooperating group of rotation means. Where a group of rotation means is used, this requires physical interlocking of the cooperating rotation means so that they may be operated by single power means and under the control of a single operator. Otherwise, the operation of the enclosure means in this tandem arrangement will be as described above. Alternately, a plurality of enclosure means may be disposed within a single rotation means. This would only require that the seal means and injection means have mirror image arrangements for receiving an enclosure means in the lowermost part and an enclosure means in the uppermost part of the mirror image arrangements. This will allow, quite easily, a tandem of two enclosure means. Yet further, a plurality of enclosure means may be stacked upon each other where the enclosure means are generally in the arrangement of FIG. 1 and a common injector means passes through the seal means of each of the enclosure means (with the exception of, of course, the last under enclosure means). By use of spacers to position the enclosure means along this common injector means, a single control means may be used for performing all of the functions of the plurality of enclosure means.

Other modifications and alternatives of the present apparatus and process will be further apparent to those skilled in the art, beyond those mentioned above. Thus, the present specification and claim luggage are intended to embrace those above-noted and further alternate embodiments as well as other obvious embodiments. Thus, the scope of the invention is to the extent of the annexed claims.

What is claimed is:
1. A centrifuge apparatus for separating and washing blood cells comprising:
   1. enclosure means for enclosing a quantity of liquid suspended blood cells,
   2. rotation means for rotating the enclosure means about the longitudinal axis thereof;
   3. injector means for moving suspended blood cells and liquids into and out of said enclosure;
   4. seal means for sealing the injector means to the enclosure means in a liquid-tight relationship;
   5. a plurality of angularly shaped blood cell receiving means in fluid communication with each other and evenly spaced about the longitudinal periphery of the enclosure means and forming a part of the enclosure means, wherein at least one pair of opposite wall portions of each of the said receiving means converge towards the longitudinal periphery of the enclosure means and thereby forming a locus of maximum centrifugal force in the rotating enclosure at the apexes formed by the juncture of the converging wall portions;
   6. a plurality of independent conduit means in fluid communication with each other, each with one end thereof in fluid communication with the said injector means and the other end thereof connected to the said locus of maximum centrifugal force;
   7. power means for rotating the rotation means and enclosure means to a speed of angular rotation sufficient to separate the blood cells from the suspending liquid and compact the blood cells in the blood cell receiving means; and
   8. control means for controlling liquid flows through the said injector means, conduit means, blood cell receiving means and enclosure means for flowing suspended blood cells into each of the blood cell receiving means, for flowing a wash liquid through each of the said conduit means and then through the compacted blood cells in each of the blood cell receiving means whereby the wash liquid passes through essentially all of the compacted blood cells, for flowing a resuspending liquid into the enclosure means and into the blood cell receiving means and for flowing resuspended blood cells from each of the said receiving means through each, respective, conduit means, through the injector means and out of the centrifuge apparatus.

2. The apparatus of claim 1 wherein the enclosure means is constructed of an inert material which is releasably held in the rotation means.

3. The apparatus of claim 2 wherein the rotation means has a cavity therein for receiving and retaining the enclosure means during rotation thereof.

4. The apparatus of claim 3 wherein the rotation means and enclosure means are complimentarily shaped so that the enclosure means may be periodically removed from the rotation means and replaced by a new enclosure means.

5. The apparatus of claim 4 wherein the enclosure means, conduit means and sealing means form a replaceable and disposable unitary structure.

6. The apparatus of claim 5 wherein the said unitary structure is made principally of a polymeric material.

7. The apparatus of claim 6 wherein the polymeric material is selected from a polyolefin, polyvinyl chloride, polyvinylidene chloride, polyvinyl acetate, polystyrene, polyacrylate, polyester, polyamide, polysilicone, polycarbonate, polyacetate or butyrate, natural or synthetic rubbers and combination thereof.

8. The apparatus of claim 7 wherein the polymeric material is extendable.

9. The apparatus of claim 8 wherein the shape of the unitary structure is conformed to the shape of the cavity in the rotation means by action of centrifugal forces acting on the unitary structure during rotation thereof.

10. The apparatus of claim 1 wherein a stack of two or more of the said enclosure means are rotated with a single rotation means.

11. A centrifuge apparatus for separating suspended, finely-divided particulate material comprising:
   1. enclosure means for enclosing a quantity of liquid suspended particulate material;
   2. rotation means for rotating the enclosure means about the longitudinal axis thereof;
   3. injector means for moving suspended finely-divided particulate material and liquids into and out of the said enclosure;

4. seal means for sealing the injector means to the enclosure means in a liquid-tight relationship;
5. a plurality of angularly shaped particulate material receiving means in fluid communication with each other and evenly spaced about the longitudinal periphery of the enclosure means and forming a part of the enclosure means, wherein at least one pair of opposite wall portions of each of the said receiving means converge towards the longitudinal periphery of the enclosure means and thereby forming a locus of maximum centrifugal force in the rotating enclosure at the apexes formed by the juncture of the converging wall portions;
6. a plurality of independent conduit means in fluid communication with each other, each with one end thereof in fluid communication with the said injector means and the other end thereof connected to the said locus of maximum centrifugal force;
7. power means for rotating the rotation means and enclosure means to a speed of angular rotation sufficient to separate the particulate material from the suspending liquid and compact the particulate material in the particulate material receiving means; and
8. control means for controlling liquid flows through the said injector means, conduit means, particulate material receiving means and enclosure means for flowing suspended particulate material into each of the particulate material receiving means, for flowing a resuspending liquid into the material receiving means and for flowing resuspended particulate material from each of the said receiving means, through each, respective, conduit means, through the injector means and out of the centrifuge apparatus.

12. The apparatus of claim 11 wherein the control means also functions to flow a wash liquid through each of the conduit means and then through the particulate material in each of the particulate material receiving means as a step intermediate the step of flowing the suspended particulate material into the receiving means and the step of flowing the resuspended particulate material from the receiving means, whereby the wash liquid passes through essentially all of the particulate material.

13. The apparatus of claim 11 wherein the enclosure means is constructed of an inert material which is releasably held in the rotation means.

14. The apparatus of claim 11 wherein the rotation means has a cavity therein for receiving and retaining the enclosure means during rotation thereof.

15. The apparatus of claim 14 wherein the rotation means and enclosure are complimentarily shaped so that the enclosure means may be periodically removed from the rotation means and replaced by a new enclosure means.

16. The apparatus of claim 15 wherein the enclosure means, conduit means and sealing means form a replaceable and disposable unitary structure.

17. The apparatus of claim 16 wherein the said unitary structure is made principally of a polymeric material.

18. The apparatus of claim 17 wherein the polymeric material is selected from a polyolefin, polyvinyl chloride, polyvinylidene chloride, polyvinyl acetate, polystyrene, polyacrylate, polyester, polyamide, polysilicone, polycarbonate, polyacetate or butyrate, natural or synthetic rubbers and combination thereof.

19. The apparatus of claim 18 wherein the polymeric material is extendable.

20. The apparatus of claim 19 wherein the shape of the unitary structure is conformed to the shape of the cavity in the rotation means by action of centrifugal forces acting on the unitary structure during rotation thereof.

21. The apparatus of claim 11 wherein a stack of two or more of the said enclosure means are rotated with a single rotation means.

22. A method for washing blood comprising:
1. flowing blood from a blood supply through a plurality of independent conduits in fluid communication with each other and into an enclosure having a plurality of angularly shaped blood cell receiving compartments in fluid communication with each other and evenly spaced about the longitudinal periphery of the enclosure and wherein at least one pair of opposite wall portions of each of the compartments converge towards the longitudinal periphery of the enclosure, the first ends of the said conduits being in fluid communication with the said blood supply and the other ends thereof being connected with apexes formed by the juncture of the said converging wall portions of each of the compartments;
2. rotating the enclosure at a speed of angular rotation such that sufficient centrifugal force is exerted on the blood whereby the blood cells are separated from the liquid portion of the blood and the blood cells are compacted into the said compartments;
3. flowing a wash liquid from a wash liquid supply source, in fluid communication with the first ends of the conduits, through the said conduits, into the apexes of the converging wall portions of the compartments, whereby the wash liquid passes through essentially all of the compacted blood cells and through the enclosure;
4. continuing the flow of wash liquid until the blood cells are washed substantially free of contaminants; and
5. reducing the angular speed of rotation of the enclosure, flowing blood cell suspending liquid into the enclosure, resuspending the blood cells in the suspending liquid and flowing the suspended blood cells through the conduit and into a collecting reservoir.

23. The method of claim 22 wherein a stack of two or more of the said enclosure means are rotated with a single rotation means and the said method is simultaneously carried out with each enclosure in the stack.

24. A method for separating suspended, finely-divided particulate material from a suspending liquid comprising the steps of:
1. flowing liquid suspended particulate material from a supply thereof through a plurality of independent conduits in fluid communication with each other and into an enclosure having a plurality of angularly shaped particulate material receiving compartments in fluid communication with each other and evenly spaced about the longitudinal periphery of the enclosure and wherein at least one pair of opposite wall portions of each of the compartments converge towards the longitudinal periphery of the enclosure, the first ends of the said conduits being in fluid communication with the said suspended particulate material supply and the other ends thereof being connected with apexes formed by the juncture of the said converging wall portions of each of the compartments;
2. rotating the enclosure at a speed of angular rotation such that sufficient centrifugal force is exerted on the suspended particulate material whereby the particulate material is separated from the suspending liquid and the particulate material is compacted into the said compartments; and
3. reducing the angular speed of rotation of the enclosure, flowing suspending liquid into the enclosure, resuspending the particulate material in the suspending liquid and flowing the suspending particulate material through the conduit and into a collecting reservoir.

25. The method of claim 24 wherein between steps 2 and 3, a wash liquid is flowed from a wash liquid supply source, in fluid communication with the first ends of the conduits, through the conduits, into the apexes of the converging wall portions of the compartments, whereby the wash liquid passes through essentially all of the compacted particulate material and through the enclosure to wash the particulate material.

26. The method of claim 24 wherein a stack of two or more of the said enclosure means are rotated with a single rotation means and the said method is simultaneously carried out with each enclosure in the stack.

* * * * *

UNITED STATES PATENT AND TRADEMARK OFFICE
CERTIFICATE OF CORRECTION

PATENT NO. : 3,982,691

DATED : September 28, 1976

INVENTOR(S) : Charles A. Schlutz

It is certified that error appears in the above-identified patent and that said Letters Patent are hereby corrected as shown below:

IN THE HEADING:

After the statement of the inventor, insert

--[73] Assignee: Union Carbide Corporation
New York, New York --

Signed and Sealed this

Eighth Day of August 1978

[SEAL]

Attest:

RUTH C. MASON
Attesting Officer

DONALD W. BANNER
Commissioner of Patents and Trademarks